United States Patent [19]

Adam et al.

[11] Patent Number: 4,970,064

[45] Date of Patent: Nov. 13, 1990

[54] ORAL COMPOSITIONS

[75] Inventors: Unus S. Adam, Birkenhead; Graham T. Brown, Wirral; Ian G. Lyle, Deeside; Michael J. Parkington, Wirral, all of Great Britain

[73] Assignee: Chesebrough Pond's USA Co., a division of Conopco, Inc., Greenwich, Conn.

[21] Appl. No.: 432,703

[22] Filed: Nov. 7, 1989

[30] Foreign Application Priority Data

Nov. 10, 1988 [GB] United Kingdom ................ 8826333

[51] Int. Cl.$^5$ .............................................. A61K 7/16
[52] U.S. Cl. ........................................ 424/49; 424/52
[58] Field of Search ............................................ 424/49

[56] References Cited

U.S. PATENT DOCUMENTS 4,296,084 10/1981 Matsushima et al. ................ 424/59

Primary Examiner—Shep K. Rose
Attorney, Agent, or Firm—Milton L. Honig

[57] ABSTRACT

The invention relates to an oral composition for the care of the mouth to inhibit oral bacteria and to neutralize acids, produced by oral bacteria. This achieved by inclusion in the oral composition of a hydrotalcite-like material of a particular general formula, typical representatives being zinc aluminum hydrotalcite ($Zn_{12}Al_6(OH)_{36}(NO_3)_6H_2O$) and copper magnesium aluminum hydrotalcite ($Cu_3Mg_9Al_4(OH)_{32}Cl_4H_2O$).

These hydrotalcite-like materials show significant antiplaque activity. Typical examples of oral compositions are toothpastes and mouth rinses.

7 Claims, No Drawings

ORAL COMPOSITIONS

This invention relates to oral compositions containing an analogue of a compound of the formula $Mg_6Al_2(OH)_{16}CO_3 4H_2O$ in any crystallographic form, and for convenience referred to hereinafter as a hydrotalcite-like compound.

It is already known from U.S. Pat. No. 4,296,094 (Kyowa Chemical Industry) to include certain magnesium aluminium hydrotalcite-like compounds in a dental cleaning composition. The compounds are said to be very effective in removing bacteria in the oral cavity which may cause dental caries. The hydrotalcite-like compounds are said to react with acids such as lactic acid which may be produced by these bacteria in the oral cavity to neutralise them.

The present invention concerns the use of other hydrotalcite-like compounds in oral compositions.

The hydrotalcite-like compounds useful in the oral compounds of the present invention can be described by the following formula:

$$M_m N_{n+p}(OH)_{2(m+n+p)} A_z{}^{y-} x H_2O$$

where:
M is any 2+ cation or combination of 2+ cations
N is any 3+ or 4+ cation or combination of 3+ and/or 4+ cations
with the proviso that M is not solely Mg when N is solely aluminium, and where
m is sum of the individual mole fractions of the 2+ cations
n is sum of the individual mole fractions of the 3+ cations
p is sum of the individual mole fractions of the 4+ cations
where either but not both of n and p can be zero, $m+n+p=1$ and $0 < n+p \leq m$
$A_z{}^{y-}$ is any anion of charge $y-$ and mole fraction z, or combination of anions of similar or different $y-$ and (the sum of the mole fraction)x(the charge on the anion) is given by the expression $$\sum_{i=1 \to t} Y_i Z_i = n + 2p$$

where t is the total number of anions
and x can range from 0 to 100.

The hydrotalcite-like compounds employed in the oral compositions of this invention are effective in inhibiting bacteria and neutralising acids produced by oral bacteria.

Examples of the 2+ cations M in the above formula are $Mg^{2+}$, $Zn^{2+}$, $Fe^{2+}$, $Cu^{2+}$, $Sn^{2+}$, $Ca^{2+}$ and $Sr^{2+}$. Suitable N cations include $Al^{3+}$, $Fe^{3+}$, $Ti^{4+}$ and $Sn^{4+}$.

Preferred divalent cations are those having bacteriostatic properties such as $Zn^{2+}$, $Cu^{2+}$ or $Sn^{2+}$ or a combination of these ions, or a combination thereof with other divalent cations. Such hydrotalcite-like compounds are advantageous in that by absorbing onto oral tissue the bacteriostatic $M^{2+}$ ions are released during slow dissolution of the hydrotalcite-like compound in oral fluids and are effective in combating the growth of dental plaque. This dissolution occurs locally in the more acidic environment created by bacterial metabolism. Most preferred as the bacteriostatic cation are zinc and copper.

The anion A may be an inorganic or organic anion. Preferred inorganic anions A are $F^-$, $Cl^-$, $NO_3^-$, $SO_4^{2-}$, $FPO_3^{2-}$, $CO_3^{2-}$ and $OH^-$. The $F^-$ and $FPO_3^{2-}$ anions have anti-caries properties and may exchange for anions found in saliva such as $Cl^-$ and $PO_4^{3-}$. Examples of organic anions are carboxylate ions such as citrate.

Preferred hydrotalcite-like compounds of this invention are:

$Zn_{12}Al_6(OH)_{36}(NO_3)_6\ H_2O$
$Zn_{12}Fe_6(OH)_{36}F_6\ H_2O$
$Cu_3Mg_9Al_4(OH)_{32}Cl_4\ H_2O$
$Cu_3Zn_9Al_4(OH)_{32}(FPO_3)_2\ H_2O$
$Sn^{II}{}_3Zn_9Sn^{IV}{}_4(OH)_{32}(CO_3)_4\ H_2O$
$Sn^{II}{}_3Mg_9Ti^{IV}{}_4(OH)_{32}(F)_8\ H_2O$
$Zn_6Al_2(OH)_{16}CO_3\ 4\ H_2O$
$Zn_8Ti_2(OH)_{22}CO_3\ 4\ H_2O$

The hydrotalcite-like compound is present in the oral composition of the invention in combination with a suitable diluent or carrier. For example the composition may be a mouthwash or toothpaste. The amount of the hydrotalcite-like compound is desirably present in an amount of at least about 0.01% up to about 30% by weight although greater amounts may be used. Preferred amounts are from 0.1% to 15% by weight of the oral composition.

The oral composition of this invention will contain other ingredients commonly used to formulate such products, depending on the form of the oral product. For instance, in the case of an oral composition in the form of a toothpaste the product will comprise a particulate abrasive cleaning agent, an humectant-containing liquid phase and a binder or thickener which acts to maintain the particulate solid abrasive in stable suspension in the liquid phase. A surfactant and a flavouring agent are also usual ingredients of commercially acceptable toothpastes.

Particulate solid abrasive cleaning agents commonly present in toothpastes include silica, alumina, hydrated alumina, calcium carbonate, anhydrous dicalcium phosphate, dicalcium phosphate dihydrate and water-insoluble sodium metaphosphate. The amount of abrasive agent is usually between about 5% and 70% by weight of the toothpaste.

Humectants commonly used are glycerol and sorbitol syrup (usually comprising an approximately 70% solution). However, other humectants are known to those in the art including propylene glycol, lactitol, xylitol and hydrogenated corn syrup. The amount of humectant will generally range from about 10% to 85% by weight of the dentifrice. The remainder of the liquid phase will consist substantially of water.

Likewise numerous binding or thickening agents have been indicated ±or use in dentifrices, preferred ones being hydroxyethylcellulose, sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binders may be used. The amount of binder included in a dentifrice is generally between 0.1% and 10% by weight.

It is usual to include a surfactant in a dentifrice and again the literature discloses a wide variety of suitable materials. Surfactants which have found wide use in practice are sodium lauryl sulphate, sodium dodecylbenzene sulphonate and sodium lauroylsarcosinate.

Other anionic surfactants may be used as well as other types such as cationic, amphoteric and non-ionic surfactants. Surfactants are usually present in an amount of form 0.5% to 5% by weight of the dentifrice.

Flavours that are usually used in dentifrices are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a dentifrice.

The oral composition of the invention may include a wide variety of optional ingredients. These include sweetening agent such as saccharin; an opacifying agent, such as titanium dioxide; a preservative, such as formalin; a colouring agent; or pH controlling agent such as an acid, base or buffer, such as benzoic acid. Furthermore, they may include anti-caries agents such as sodium fluoride, stannous fluoride, monosodium fluorophosphate; anti-plaque agents such as stannous pyrophosphate, zinc citrate; antibacterial agents such as 2,4,4'-trichloro-2'-hydroxy-diphenylether, anti-calculus agents such as alkali metal pyrophosphates and so on.

For a fuller discussion of the formulation of oral compositions reference is made to Harry's Cosmeticology, Seventh Edition, 1982, Edited by J B Wilkinson and R J More, pages 609 to 617.

The invention also provides a method of treating the oral cavity with the above hydrotalcite-like compounds. The treatment may comprise rinsing with a suspension of the hydrotalcite-like compound in water or with a flavored mouthwash product containing the hydrotalcite-like compound or by brushing the teeth with a dental product comprising the hydrotalcite-like compound.

Methods for the preparation of hydrotalcite-like compounds are known and have been described in a number of publications including Solid States Ionics 22 (1986) pages 135–141 where there is published a paper by Walter T Reichle entitled "Synthesis of Anionic Clay Minerals (Mixed Metal Hydroxides, Hydrotalcite)".

The zinc hydrotalcite for inclusion in the oral compositions illustrated below may be prepared in the following way.

250mls of distilled water are added to a 1 liter reaction vessel. A mixture of $Zn(NO_3)_2 6H_2O$ (60 g, 0.2 mol) and $Al(NO_3)_3 9H_2O$ (30 g, 0.075 mol) in one beaker and NaOH (30 g, 0.75 mol) in another (both made up to 200 mls with distilled water) are added via two peristaltic pumps over a period of 30 minutes. The reaction is continuously stirred by means of an overhead paddle stirrer, and the pH is maintained at pH 10±0.2 by controlling the rate of NaOH addition. The precipitate formed is aged at 95° C. for 24 hours in polythene pots after which the product is filtered, washed with distilled water and dried. The zinc hydrotalcite obtained has the formula $Zn_{12}Al_6(OH)_{36}(NO_3)_6H_2O$.

By ion exchange the nitrate anion may be exchanged for other ions such as the monofluorophosphate anion.

The following Examples illustrate oral compositions in accordance with the invention. Percentages are by weight.

EXAMPLE 1

A toothpaste is made having the following composition.

| Ingredients | % |
| --- | --- |
| Silica xerogel | 10.00 |
| Zinc hydrotalcite[1] | 15.00 |
| Sorbitol syrup (70% solution) | 50.00 |
| Polyethylene glycol MW 1500 | 5.00 |
| Sodium carboxymethyl cellulose | 0.90 |
| Sodium lauryl sulphate | 1.50 |
| Sodium saccharin | 0.30 |
| Titanium dioxide | 1.00 |
| Sodium monofluorophosphate | 1.13 |
| Flavour oil | 0.80 |
| Water to | 100.00 |

EXAMPLE 2

A toothpaste is made having the following composition.

| Ingredients | % |
| --- | --- |
| Silica xerogel | 10.00 |
| Silica aerogel | 7.50 |
| Zinc hydrotalcite[1] | 10.00 |
| Sorbitol syrup (70% solution) | 55.00 |
| Hydroxyethylcellulose | 0.93 |
| Tween 80 | 1.50 |
| Sodium saccharin | 0.30 |
| Titanium dioxide | 1.00 |
| Sodium fluoride | 0.33 |
| Flavour oil | 1.00 |
| Water to | 100.00 |

The following experiments illustrate the acid buffering effect and release of soluble zinc from zinc hydrotalcite.

Buffering Effect of Zinc Hydrotalcite

The following data correspond to the addition of 0.2 g of a zinc-aluminium hydrotalcite (formula $Zn_{12}Al_6(O)_{36}(NO_3)_6H_2O$) to 50 mls of hydrochloric acid (0.01 M) (Table 1) or sodium hydroxide solution ($10^{-4}$ M) (Table 2).

TABLE 1

| Time/minutes | 0 | 1.0 | 1.5 | 2.0 | 3.0 | 5.0 | 10.0 |
| --- | --- | --- | --- | --- | --- | --- | --- |
| pH - after addition of Zn hydrotalcite | 2.0 | 3.0 | 4.0 | 4.4 | 4.5 | 4.6 | 5.7 |

TABLE 2

| Time/minutes | 0 | 0.5 | 2.0 | 3.0 | 10.0 | 15.0 |
| --- | --- | --- | --- | --- | --- | --- |
| pH - after addition of Zn hydrotalcite | 10.1 | 7.5 | 7.0 | 6.25 | 6.1 | 6.2 |

Release of Soluble Zinc from Zinc Hydrotalcite

Table 3 illustrates the amount of soluble zinc released from a dispersion of 0.2 g of Zn hydrotalcite (formula $Zn_{12}Al_6(OH)_{36}(NO_3)_6H_2O$) in 20 ml of solution at different pHs, the initial ionic strengths being kept constant at $10^{-2}$M. After 30 minutes the suspension was centrifuged and the zinc concentration in the supernatant was determined by atomic absorption spectroscopy. Hydrochloric acid and sodium hydroxide solutions were used to adjust the pH and sodium chloride used to adjust the initial ionic strength.

TABLE 3

| Initial pH | 2.12 | 2.66 | 3.47 | 5.87 | 7.50 | 9.93 | 10.23 |
| --- | --- | --- | --- | --- | --- | --- | --- |
| Concentration | 213 | 104 | 45 | 32 | 30 | 41 | 52 |

TABLE 3-continued

| Initial pH | 2.12 | 2.66 | 3.47 | 5.87 | 7.50 | 9.93 | 10.23 |
|---|---|---|---|---|---|---|---|
| of soluble zinc (ppm) | | | | | | | |

EXAMPLE 3

The zinc hydrotalcite of the formula $Zn_6Al_2(OH)_{16}CO_3.4H_2O$ and the copper hydrotalcite of the formula $Cu_3Mg_9Al_4(OH)_{32}Cl_4H_2O$ were tested as to their antiplaque activity. The test protocol was as follows: Strep.sanguis cells were grown overnight on blood agar plates. The cells were harvested and suspended in sterile 1% calcium chloride. Hydroxyapatite discs were immersed in this bacterial suspension for 30 mins, then transferred to an in vitro plaque apparatus. Medium (BHI +1% sucrose) was dripped onto the discs continuously for 24 hrs at 37° C.

Test solutions were prepared by dispersing the appropriate solid material at a concentration of 1% w/w in distilled water or in water containing 0.2% Natrosol 250 HR (a polymeric thickening agent). They were sterilised by autoclaving before use.

Sterile solutions of test products were applied to the discs (2.5 ml/disc), then a suspension of Strep.sanguis in water was used to re-inoculate each disc. The medium drip was re-started and the discs incubated for a further 24 hrs at 37° C. The amount of plaque growth was assessed by sonicating each disc for 20 secs in 2 ml of saline solution and measuring total viable counts. (TVC)

The results were as follows:

| The results were as follows: Test solution (n = 4) | TVC (cfu/ml) |
|---|---|
| Distilled water (control) | $2.5 (\pm 0.45) \times 10^7$ |
| Zinc hydrotalcite | $1.05 (\pm 1.3) \times 10^6$ |
| Copper hydrotalcite (+ Natrosol) | $5.8 (\pm 2.6) \times 10^3$ |

We claim:

1. An oral toothpaste or mouthwash composition for removing oral bacteria and neutralizing acids produced by oral bacteria comprising at least one toothpaste or mouthwash excipient and from 0.01% to 30% by weight of a hydrotalcite-like material of the following formula:

$$M_m N_{n+p}(OH)_{2(m+n+p)} A_z^{Y-} xH_2O$$

where:
   M is any 2+ bacteriostatic cation or combination of 2+ bacteriostatic cations
   N is any 3+ or 4+ cation or combination of 3+ and/or 4+ cations
with the proviso that M is not solely Mg when N is solely aluminum, and where
   m is sum of the individual mole fractions of the 2+ cations
   n is sum of the individual mole fractions of the 3+ cations
   p is sum of the individual mole fractions of the 4+ cations
where either but not both of n and p can be zero, $m+n+p=1$ and $0 < n+p \leq m$
$A_z^{y-}$ is any anion of charge $y-$ and mole fraction z, or combination of anions of similar or different $y-$ and (the sum of the mole fraction) times (the charge on the anion) is given by the expression $$\sum_{i=1 \to t} Y_i Z_i = n + 2p$$

where t is the total number of anions and x can range from 0 to 100.

2. An oral toothpaste or mouthwash composition according to claim 1, wherein M is $Mg^{2+}$, $Zn^{2+}$, $Fe^{2+}$, $Cu^{2+}$, $Sn^{2+}$, $Ca^{2+}$, $Sr^{2+}$ or a combination of two of these cations, and N is $Al^{3+}$, $Fe^{3+}$, $Ti^{4+}$, $Sn^{4+}$ or a combination of these cations.

3. An oral toothpaste or mouthwash composition according to claim 1 wherein M is $Zn^{2+}$, $Cu^{2+}$, $Sn^{2+}$ or a combination thereof.

4. An oral toothpaste or mouthwash composition according to claim 1, wherein A is $F^-$, $Cl^-$, $NO_3^-$, $SO_4^{2-}$, $FPO_3^{2-}$, $CO_3^{2-}$, citrate and $OH^-$.

5. An oral toothpaste or mouthwash composition according to claim 1, wherein the hydrotalcite-like material comprises one or more of the following compounds:
   $Zn_{12}Al_6(OH)_{36}(NO_3)_6\ H_2O$
   $Zn_{12}Fe_6(OH)_{36}F_6\ H_2O$
   $Cu_3Mg_9Al_4(OH)_{32}Cl_4\ H_2O$
   $Cu_3Zn_9Al_4(OH)_{32}(FPO_3)_2\ H_2O$
   $Sn^{II}_3Zn_9Sn^{IV}_4(OH)_{32}(CO_3)_4\ H_2O$
   $Sn^{II}_3Mg_9Ti^{IV}_4(OH)_{32}(F)_8\ H_2O$
   $Zn_6Al_2(OH)_{16}CO_3\ 4\ H_2O$
   $Zn_8Ti_2(OH)_{22}CO_3\ 4\ H_2O$ 6. An oral zinc hydrotalcite composition according to claim 1, formulated in the form of a toothpaste or a mouthrinse composition.

7. Method for treating the oral cavity to remove oral bacteria and to neutralize acids, produced by oral bacteria, characterised in that the oral cavity is treated with a composition according to claim 1.

* * * * *